United States Patent [19]

Iizuka et al.

[11] Patent Number: 4,638,087
[45] Date of Patent: Jan. 20, 1987

[54] 6-SUBSTITUTED NAPHTHALENE-2-CARBOXYLIC ACIDS AND PROCESS FOR PRODUCING THE SAME

[75] Inventors: Akira Iizuka; Yutaka Konai; Takashi Yamauchi; Shoichiro Hayashi, all of Iwaki, Japan

[73] Assignee: Kureha Kagaku Kogyo Kabushiki Kaisha, Tokyo, Japan

[21] Appl. No.: 838,525

[22] Filed: Mar. 11, 1986

[51] Int. Cl.$^4$ .............................................. C07C 63/34
[52] U.S. Cl. .................................................. 562/467
[58] Field of Search ........................................ 562/467

[56] References Cited

U.S. PATENT DOCUMENTS 4,374,262  2/1983  McGinnis ........................... 562/467

FOREIGN PATENT DOCUMENTS 737492  6/1966  Canada ................................. 562/467

Primary Examiner—Paul J. Killos
Attorney, Agent, or Firm—John P. White

[57] ABSTRACT

Disclosed herein are the novel 6-substituted naphthalene-2-carboxylic acids represented by the formula (I):

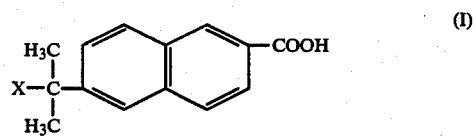

wherein X represents a hydroperoxy group or a hydroxy group, and a process for producing the 6-substituted naphthalene-2-carboxylic acid represented by the formula (I) by reacting 6-isopropylnaphthalene-2-carboxylic acid with molecular oxygen under heating in the presence of a salt of persulfuric acid as a catalyst in an aqueous alkaline solution.

8 Claims, 5 Drawing Figures

6-SUBSTITUTED NAPHTHALENE-2-CARBOXYLIC ACIDS AND PROCESS FOR PRODUCING THE SAME

BACKGROUND OF THE INVENTION

The present invention relates to novel 6-substituted naphthalene-2-carboxylic acids represented by the formula (I):

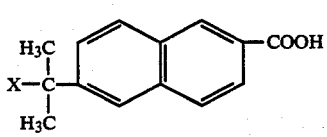

wherein X represents a hydroperoxy group or a hydroxy group, and a process for producing the same.

The 6-substituted naphthalene-2-carboxylic acids are useful compounds as intermediates for producing a polymer of 6-hydroxynaphthalene-2-carboxylic acid, which has attracted attention in recent years as a high polymeric material for producing molded articles such as fibers, etc., because the polymer of 6-hydroxynaphthalene-2-carboxylic acid shows excellent high elasticity, high tensile strength and high heat resistance. Namely, 6-hydroxynaphthalene-2-carboxylic acid, which is a monomer for the above polymer, is easily obtainable by subjecting the 6-substituted naphthalene-2-carboxylic acid to acid decomposition.

As the method for producing 6-hydroxynaphthalene-2-carboxylic acid, the following methods have been hitherto known.

(i) A method comprises reacting potassium salt of β-naphthol with gaseous carbon dioxide at a high temperature under a high pressure (refer to U.S. Pat. Nos. 1,593,816; 4,287,357; 4,345,095; 4,329,494 and 4,345,094), (ii) A method comprises reacting potassium salt of β-naphthol with gaseous carbon dioxide in a medium of high boiling point at a high temperature and under a high pressure (refer to Japanese Patent Applications Laying-Open (KOKAI) No. 57-95939 (1982) and No. 58-99436 (1983)), and (iii) A method comprises reacting 6-bromo-2-naphthol with carbon monoxide in methanol (refer to Japanese Patent Application Laying-Open (KOKAI) No. 57-91955 (1982)).

However, the above-mentioned methods have the respective defects as follows.

(a) The production cost in the methods (i), (ii) and (iii) are high due to the expensive production apparatus, because it is necessary to carry out the reaction of the methods (i) and (ii) at a high temperature range of 260° to 280° C. and also the reaction of the method (iii) under a high pressure of up to 70 kg/cm².

(b) Large amount of by-product such as β-naphthol in the methods of (i) and (ii) complicates the processes because of the necessity of removal of β-naphthol in an after-treatment.

(c) Since the production of an unnecessary isomer of 6-hydroxynaphthalene-2-carboxylic acid such as 3-hydroxynaphthalene-2-carboxylic acid is inevitable, there are problems of the difficulty in separating the isomers and of the reduction in the yield of the objective compound.

In addition to these defects, the objective compound is produced in a low yield by the above-mentioned known methods, for instance, around 26.5% in the method (i), around 45% in the method (ii) and around 37% in the method (iii) and accordingly, none of the three methods are suitable for manufacturing the objective product in a large scale.

In an attempt to pursue industrially advantageous methods for producing 6-hydroxynaphthalene-2-carboxylic acid, the inventors have succeeded in the synthesis of methyl 6-(2-hydroperoxy-2-propyl)naphthalene-2-carboxylate as an intermediate for producing 6-hydroxynaphthalene-2-carboxylic acid. Namely, methyl 6-(2-hydroperoxy-2-propyl)naphthalene-2-carboxylate can be obtained in a high yield by oxidizing methyl 6-isopropylnaphthalene-2-carboxylate in the presence of a cobalt or manganese salt of an organic acid as a catalyst (refer to Japanese Patent Application Laying-Open (KOKAI) No. 60-243063 (1985)).

However, in order to oxidize the isopropyl group of 6-isopropylnaphthalene-2-carboxylic acid, it is necessary to use the compound in which the carboxylic group at 2-position has been esterified, as the starting material.

Accordingly, as a result of further study of the oxidation of isopropyl group of 6-isopropylnaphthalene-2-carboxylic acid, the present inventors have found novel compounds, 6-(2-hydroperoxy-2-propyl)naphthalene-2-carboxylic acid and 6-(2-hydroxy-2-propyl)naphthalene-2-carboxylic acid obtained by directly oxidizing the isopropyl group of 6-isopropylnaphthalene-2-carboxylic acid without preliminarily esterifying the carboxylic group at 2-position of 6-isopropylnaphthalene-2-carboxylic acid. Furthermore, the present inventors have found that 6-hydroxynaphthalene-2-carboxylic acid can be obtained profitably at a high purity by subjecting each or both of the above-mentioned two novel compounds to acid decomposition, and based on these findings, the present invention has been attained.

SUMMARY OF THE INVENTION

In a first aspect of the present invention, there is provided 6-substituted naphthalene-2-carboxylic acid represented by the formula (I):

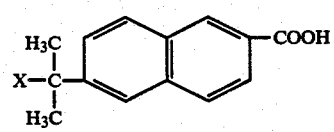

wherein X represents a hydroperoxy group or a hydroxy group.

In a second aspect of the present invention, there is provided a process for producing 6-substituted naphthalene-2-carboxylic acid represented by the formula (I):

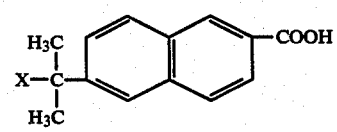

wherein X represents a hydroperoxy group or a hydroxy group, comprising the step of reacting 6-isopropylnaphthalene-2-carboxylic acid with molecular oxygen at a temperature range of 50° to 90° C. in the presence of a salt of persulfuric acid as a catalyst in an aqueous alkaline solution.

BRIEF EXPLANATION OF DRAWINGS

Of the attached drawings.

DETAILED DESCRIPTION OF THE INVENTION

The characteristic of the present invention lies in the 6-substituted naphthalene-2-carboxylic acid represented by the formula (I):

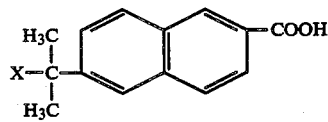
(I)

wherein X represents a hydroperoxy group or a hydroxy group, namely 6-(2-hydroperoxy-2-propyl)naphthalene-2-carboxylic acid represented by the formula (II):

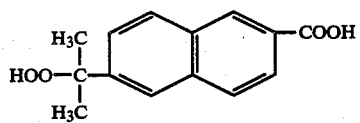
(II)

or 6-(2-hydroxy-2-propyl)naphthalene-2-carboxylic acid represented by the formula (III):

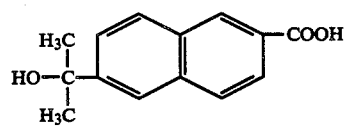
(III)

Besides, another characteristic of the present invention lies in the process for producing 6-substituted naphthalene-2-carboxylic acid represented by the formula (I) by oxidizing 6-isopropylnaphthalene-2-carboxylic acid with molecular oxygen at a temperature range of 50° to 90° C. in the presence of a salt of persulfuric acid as a catalyst in an aqueous alkaline solution.

The physicochemical properties of the novel 6-substituted naphthalene-2-carboxylic acid according to the present invention are shown in Table 1.

TABLE 1

Figure 1:
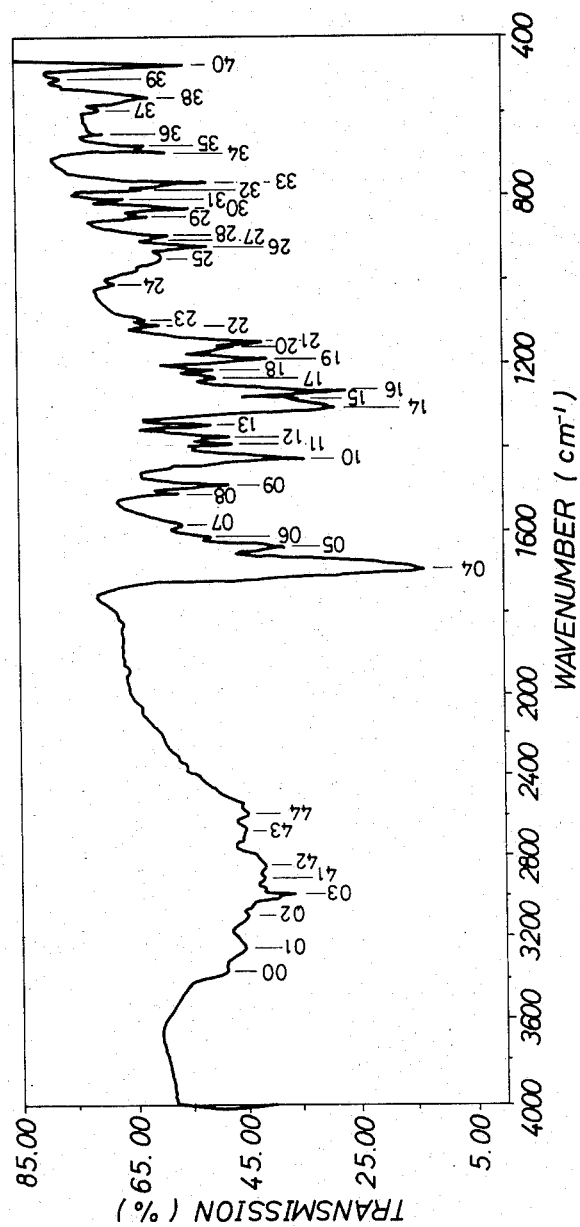
FIGS. 1 and 3 are the respective infrared absorption spectra of 6-(2-hydroperoxy-2-propyl)naphthalene-2-carboxylic acid and 6-(2-hydroxy-2-propyl)naphthalene-2-carboxylic acid.
Figure 2:
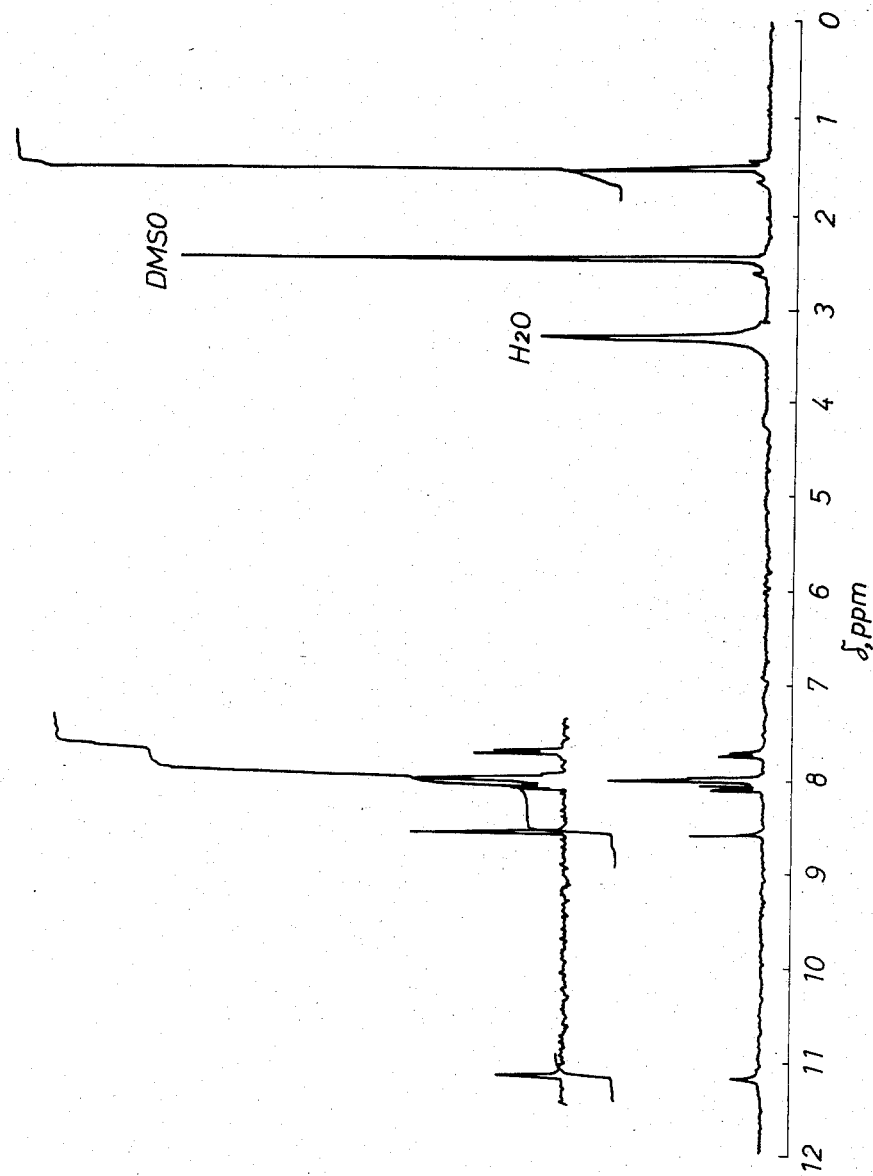
FIGS. 2 and 4 are the respective $^1$H-nuclear magnetic resonance spectra of the above-mentioned two compounds and FIG. 5 shows the result of mass spectrum analysis of 6-(2-hydroxy-2-propyl)naphthalene-2-carboxylic acid.
Figure 3:
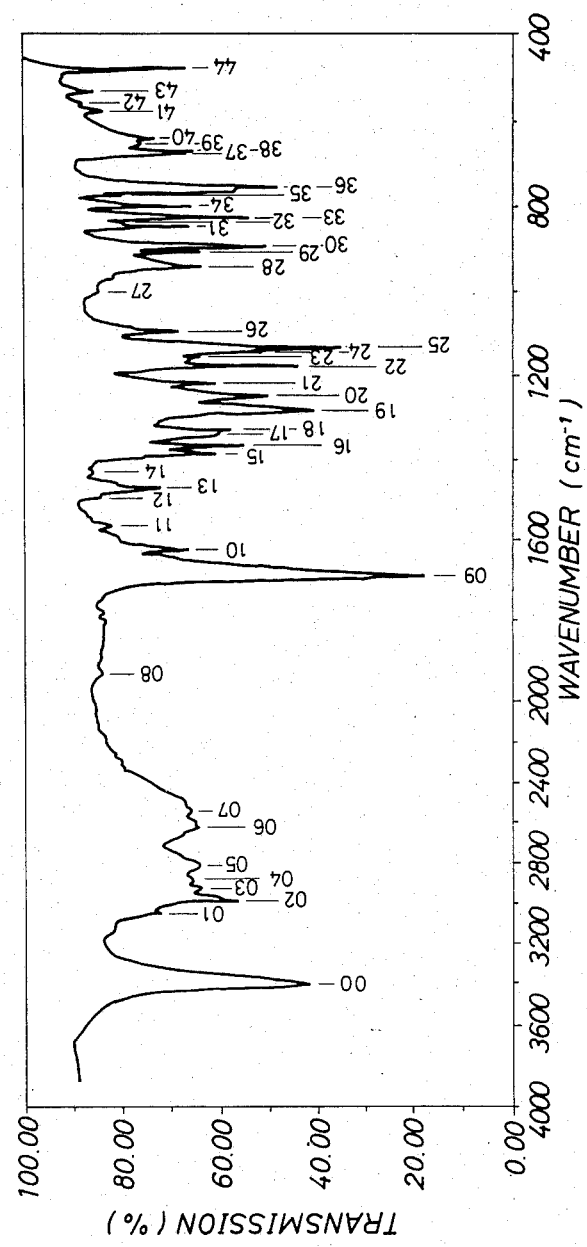
Figure 4:
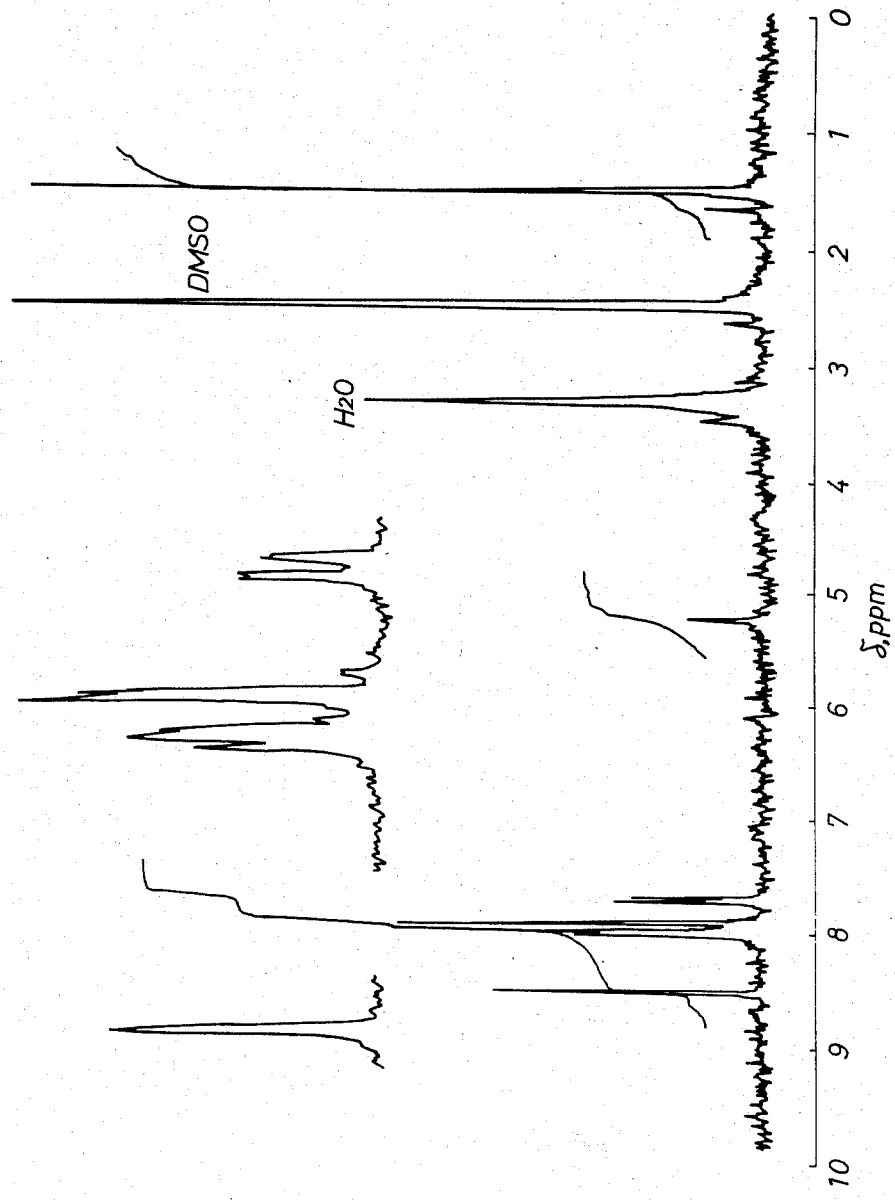
Figure 5:
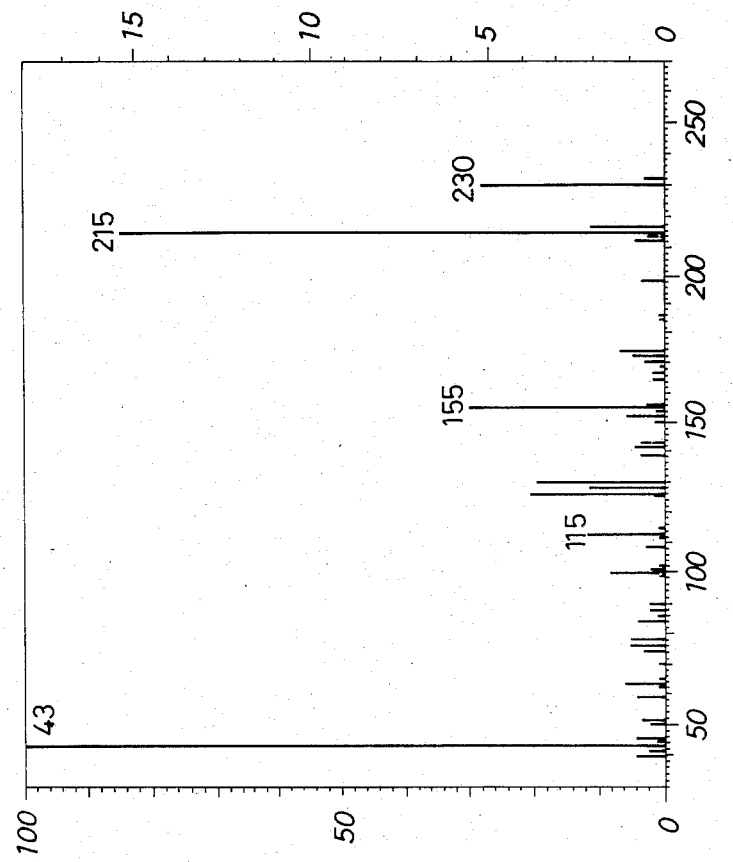

| Physicochemical property | Compound represented by Formula (II) | | Compound represented by Formula (III) | |
| --- | --- | --- | --- | --- |
| Molecular weight | 245.24 | | 229.24 | |
| Appearance | white acicular crystal | | white plate-like crystal | |
| Melting point (°C.) | 165–166 | | 204–205 | |
| Solubility | soluble in acetone, ethanol, acetonitrile, and DMSO insoluble in benzene, n-hexane, carbon tetrachloride, chloroform and water | | soluble in acetone, ethanol, acetonitrile, ether and DMSO insoluble in benzene, n-hexane, carbon tetrachloride, chloroform and water | |
| Elemental composition | Carbon (%) | Hydrogen (%) | Carbon (%) | Hydrogen (%) |
| Found | 68.0 | 5.7 | 72.2 | 6.1 |
| Calculated | 68.28 | 5.73 | 73.03 | 6.13 |
| Infrared absorption spectrum | Shown in FIG. 1 | | Shown in FIG. 3 | |
| Nuclear magnetic resonance spectrum | Shown in FIG. 2 | | Shown in FIG. 4 | |
| Mass spectral analytical data | — | | Shown in FIG. 5 | |

The process for producing 6-substituted naphthalene-2-carboxylic acid according to the present invention is explained more in detail as follows.

In the process according to the present invention, 6-isopropylnaphthalene-2-carboxylic acid is oxidized with molecular oxygen in an aqueous alkaline solution of an amount of 3 to 20 times by weight, preferably 5 to 10 times by weight of 6-isopropylnaphthalene-2-carboxylic acid at a temperature range of 50° to 90° C., preferably from 60° to 70° C. under ordinary pressure or an applied pressure for longer than 10 hours in the presence of a salt of persulfuric acid as a catalyst in an amount of 5 to 30% by weight, preferably 10 to 15% by weight of 6-isopropylnaphthalene-2-carboxylic acid. After the reaction is over, the reaction mixture is adjusted to pH 6 with a diluted mineral acid, thereby precipitating the unreacted 6-isopropylnaphthalene-2-carboxylic acid and after removing the thus precipitated acid by filtration, the pH of the filtrate is adjusted to 3.5 with a diluted mineral acid to precipitate the objective compounds, 6-(2-hydroperoxy-2-propyl)naphthalene-2-carboxylic acid and 6-(2-hydroxy-2-propyl)naphthalene-2-carboxylic acid in the same time. Namely, the objective compounds represented by the formulae (II) and (III) are obtained simultaneously.

As the aqueous alkaline solution used in the reaction, an aqueous solution of sodium carbonate, sodium hydroxide, sodium bicarbonate, potassium carbonate, potassium hydroxide and potassium bicarbonate may be exemplified, the amount thereof being 100 to 200% by equivalent, preferably from 110 to 130% by equivalent of 6-isopropylnaphthalene-2-carboxylic acid.

As a salt of persulfuric acid used as the catalyst, ammonium persulfate and potassium persulfate may be exemplified.

In addition, in the case where 6-isopropylnaphthalene 2-carboxylic acid is reacted with molecular oxygen in the aqueous alkaline solution, influence of pH of the reaction system on the reaction rate and formation of by-products are important and accordingly, the pH of the reaction system is adjusted to 7.5 to 14, preferably from 9 to 12.

The composition of the reaction mixture obtained by the process shown above depends on the reaction conditions and when the reaction is carried out at 60° C. for 20 to 30 hours, the following composition is obtained.

30 to 50 mol % of the unreacted 6-isopropylnaphthalene-2-carboxylic acid, 45 to 70 mol % of 6-(2-hydroperoxy-2-propyl)naphthalene-2-carboxylic acid and 6-(2-hydroxy-2-propyl)naphthalene-2-carboxylic acid, and 0 to 5 mol % of other material(s).

Namely, in the reaction according to the present invention, the formation of by-products is not observed or is very little.

The ratio of the compound represented by the formula (II) to the simultaneously produced compound represented by the formula (III) depends on the reaction conditions and in many cases the molar ratio of the compounds represented by the formula (II) to that represented by the formula (III) is 40–60/5–10. Of course, it is possible to reduce the ratio further by selecting the reaction conditions.

In addition, when it is necessary to separate the thus obtained two compounds simultaneously produced, they are separable from each other by a method such as inversed phase column chromatography, recrystallization, etc. However, since both 6-(2-hydroperoxy-2-propyl)naphthalene-2-carboxylic acid and 6-(2-hydroxy-2-propyl)naphthalene-2-carboxylic acid can form 6-hydroxynaphthalene-2-carboxylic acid nearly quantitatively when each of them is subjected to acid decomposition under the same conditions, the ratio of the two compounds and the separation of the thus formed two compounds are not important from the viewpoint of the usage of the two compounds as the intermediates for the production of 6-hydroxynaphthalene-2-carboxylic acid.

Namely, in the process according to the present invention, it is important that the sum of the yields of the two compounds is high and it is also important to select the reaction conditions not to form the by-product(s).

According to the process of the present invention, since both 6-(2-hydroperoxy-2-propyl)naphthalene-2-carboxylic acid and 6-(2-hydroxy-2-propyl)naphthalene-2-carboxylic acid are obtained in a high yield and with a high purity, the present invention is extremely advantageous commercially. In addition, according to the process of the present invention, both two compounds can be converted simultaneously into 6-hydroxynaphthalene-2-carboxylic acid quantitatively, and they are stable crystals soluble in many organic solvents such as acetone, ethanol, dimethylsulfoxide (referred to as DMSO), etc. and easily handled. Accordingly, both two compounds are extremely useful substances as the raw materials for commercial production of 6-hydroxynaphthalene-2-carboxylic acid.

Although hydroperoxides are generally regarded as those difficult to be handled in a large scale as the industrial raw material, because they are extremely sensitive to impact and friction as are seen in t-butylhydroperoxide and cumene hydroperoxide resulting in danger of inflammation, 6-(2-hydroperoxy-2-propyl)naphthalene-2-carboxylic acid according to the present invention is extremely stable as has been stated above, and the handling thereof is easy enough.

The present invention and the effects thereof will be explained concretely more in detail while referring to the non-limitative examples as follows.

EXAMPLE 1

Into a four-necked, 200 ml glass flask provided with a stirrer, a reflux condenser, a gas inlet tube and a thermometer, 6.25 g of sodium carbonate, 100 g of water, 10 g of 6-isopropylnaphthalene-2-carboxylic acid and 1.26 g of potassium persulfate were introduced, and pure gaseous oxygen was led into the content of the flask at a rate of 2 liters/hour while stirring thereof at a temperature of 60° C. to react the content of the flask. After 30 hours, the reaction mixture of the following composition was obtained.

6-isopropylnaphthalene-2-carboxylic acid (unreacted): 30.9 mol %

6-(2-hydroperoxy-2-propyl)naphthalene-2-carboxylic acid: 55.3 mol %

6-(2-hydroxy-2-propyl)naphthalene-2-carboxylic acid: 9.5 mol %

The analytical data given in these Examples were obtained with high-performance liquid-chromatography (hereinafter referred to as HPLC).

The pH of the thus obtained reaction mixture was adjusted to 6 by adding diluted sulfuric acid thereto to precipitate crystals, and the crystals were collected by filtration, washed with water and dried to obtain 3.55 g of white powdery material having the following composition.

84.8% by weight of unreacted 6-isopropyl-naphthalene-2-carboxylic acid.

8.7% by weight of 6-(2-hydroperoxy-2-propyl)naphthalene-2-carboxylic acid.

6.5% by weight of the other material(s).

The pH of the filtrate obtained by filtration of the above-mentioned crystals was adjusted to 3.5 by adding diluted sulfuric acid to precipitate microcrystals, which were collected by filtration, washed with water and dried. The thus obtained 6.6 g of a white powdery material had the following composition.

91.5% by weight of 6-(2-hydroperoxy-2-propyl)-naphthalene-2-carboxylic acid.

8.5% by weight of 6-(2-hydroxy-2-propyl)naphthalene-2-carboxylic acid.

The above-mentioned white powdery material consisting of 6-(2-hydroperoxy-2-propyl)naphthalene-2-carboxylic acid and 6-(2-hydroxy-2-propyl)naphthalene-2-carboxylic acid was reacted in a solvent, acetonitrile, at 50° C. for 30 minutes adding hydrogen peroxide and perchloric acid. Thus, the two compounds were simultaneously subjected to acid decomposition to form 6-hydroxynaphthalene-2-carboxylic acid nearly quantitatively.

EXAMPLE 2

Into the same flask as that used in Example 1, 6.25 g of sodium carbonate, 100 g of water, 10 g of 6-isopropylnaphthalene-2-carboxylic acid and 1.07 g of ammonium persulfate were introduced, and the content was reacted in the same manner as in Example 1. After reacting for 30 hours, the reaction mixture of the following composition was obtained.

37.0 mol % of the unreacted 6-isopropylnaphthalene-2-carboxylic acid.

48.0 mol % of 6-(2-hydroperoxy-2-propyl)naphthalene-2-carboxylic acid.

The thus obtained reaction mixture was treated in the same operation as in Example 1 to obtain 4.25 g of a white powdery material of the following composition.

87.5% by weight of the unreacted 6-isopropylnaphthalene-2-carboxylic acid.

8.5% by weight of 6-(2-hydroperoxy-2-propyl)naphthalene-2-carboxylic acid.

4.5% by weight of the other material(s).

The pH of the filtrate obtained by filtration of the above-mentioned white powdery material was adjusted to 3.5 by adding dilute sulfuric acid, and the thus precipitated crystals were collected by filtration, washed with water and dried to obtain 5.70 g of white microcrystals of the following composition.

90.5% by weight of 6-(2-hydroperoxy-2-propyl)-naphthalene-2-carboxylic acid.

9.5% by weight of 6-(2-hydroxy-2-propyl)naphthalene-2-carboxylic acid.

The thus obtained white microcrystals consisting of 6-(2-hydroperoxy-2-propyl)naphthalene-2-carboxylic acid and 6-(2-hydroxy-2-propyl)naphthalene-2-carboxylic acid were reacted in acetonitrile at 50° C. for 30 minutes in the presence of hydrogen peroxide and perchloric acid. Thus, the two compounds were subjected to acid decomposition to form 6-hydroxynaphthalene-2-carboxylic acid almost quantitatively.

What is claimed is:

1. 6-substituted naphthalene-2-carboxylic acids represented by the formula (I):

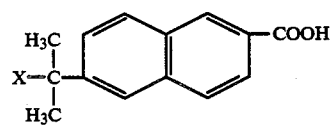
(I)

wherein X represents a hydroperoxy group or a hydroxy group.

2. 6-substituted naphthalene-2-carboxylic acid according to claim 1, wherein said X represents a hydroperoxy group.

3. 6-substituted naphthalene-2-carboxylic acid according to claim 1, wherein said X represents a hydroxy group.

4. A process for producing 6-substituted naphthalene-2-carboxylic acids represented by the formula (I):

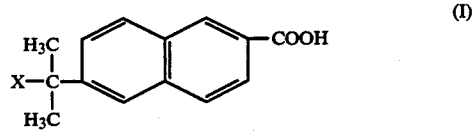
(I)

wherein X represents a hydroperoxy group or a hydroxy group, comprising the step of reacting 6-isopropylnaphthalene-2-carboxylic acid with molecular oxygen at a temperature range of 50° to 90° C. in the presence of a salt of persulfuric acid as a catalyst in an aqueous alkaline solution.

5. A process according to claim 4, wherein said catalyst is potassium persulfate or ammonium persulfate.

6. A process according to claim 4, wherein said catalyst is 5 to 30% by weight per 6-isopropylnaphthalene-2-carboxylic acid.

7. A process according to claim 4, wherein said alkali is one selected from the group consisting of sodium carbonate, sodium hydroxide, sodium bicarbonate, potassium carbonate, potassium hydroxide and potassium bicarbonate.

8. A process according to claim 4, wherein said alkali is 100 to 200% by equivalent per 6-isopropylnaphthalene-2-carboxylic acid.

* * * * *